(12) United States Patent
Cabrera

(10) Patent No.: US 9,227,099 B2
(45) Date of Patent: Jan. 5, 2016

(54) METHODS AND COMPOSITIONS FOR OXIDIZING BISPHENOL A

(75) Inventor: Robert M. Cabrera, Austin, TX (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 25 days.

(21) Appl. No.: 13/517,182

(22) PCT Filed: Dec. 19, 2011

(86) PCT No.: PCT/US2011/065934
§ 371 (c)(1),
(2), (4) Date: Jun. 19, 2012

(87) PCT Pub. No.: WO2013/095350
PCT Pub. Date: Jun. 27, 2013

(65) Prior Publication Data
US 2013/0157336 A1   Jun. 20, 2013

(51) Int. Cl.
*A62D 3/02* (2007.01)
*C12N 9/00* (2006.01)
*C12N 11/04* (2006.01)
*C12N 9/02* (2006.01)
*C12N 9/10* (2006.01)
*C12N 11/08* (2006.01)
*C08J 7/04* (2006.01)
*C09D 7/12* (2006.01)
*A62D 101/20* (2007.01)
*A62D 101/28* (2007.01)

(52) U.S. Cl.
CPC . *A62D 3/02* (2013.01); *C08J 7/047* (2013.01); *C09D 7/1233* (2013.01); *C12N 9/00* (2013.01); *C12N 9/0061* (2013.01); *C12N 9/1051* (2013.01); *C12N 9/13* (2013.01); *C12N 11/04* (2013.01); *C12N 11/08* (2013.01); *C12Y 110/03002* (2013.01); *C12Y 111/01* (2013.01); *C12Y 204/01017* (2013.01); *A62D 2101/20* (2013.01); *A62D 2101/28* (2013.01)

(58) Field of Classification Search
None
See application file for complete search history.

(56) References Cited

U.S. PATENT DOCUMENTS 4,006,271 A * 2/1977 French et al. ............. 427/164
6,180,378 B1   1/2001 Shen et al.
2010/0210745 A1  8/2010 McDaniel et al.

FOREIGN PATENT DOCUMENTS

CA        2388446         3/2001
WO   WO-2010/124084     10/2010
WO    WO 2010124084 A1 * 10/2010
WO   WO-2011/155943     12/2011

OTHER PUBLICATIONS

Hanioka et al., Chemosphere 74: 33-36 (2008).*
Jin et al., Analytica Chimica Acta 461: 1-36 (2002).*
Carwile et al., Environmental Health Perspectives 117(9): 1368-1372 (2009).*
Huang et al., "The differences in absorption and metabolism of bisphenol A between rats and mice," Zhonghua Yu Fang Yi Xue Za Zhi, (2010), 44(8): 731-735 (Abstract).*
Hwang et al., "Scratch Resistant and Transparent UV-Protective Coating on Polycarbonate," Journal of Sol-Gel Science and Technology, (2003), 26:1, 783-787.*
Lloret et al., "Immobilization of laccase by encapsulation in a sol-gel matrix and its characterization and use for the removal of estrogens," Biotechnol. Prog., (2011), 27(6): 1570-1579.*
Mitsunaga et al., "Intercalated Polycarbonate/Clay Nanocomposites: Nanostructure Control and Foam Processing," Macromol. Mater. Eng., (2003), 288:7, 543-548.*
Shimizu et al., "Sulfation of bisphenol A abolished its estrogenicity based on proliferation and gene expression in human breast cancer MCF-7 cells," Toxicol. in Vitro, (2002), 16:5, 549-556.*
Suiko et al., "Sulfation of Environmental Estrogen-like Chemicals by Human Cytosolic Sulfotransferases," Biochemical and Biophysical Research Communications, (2000), 267:7, 80-84.*
Wilson et al., "cDNA cloning, functional expression, and characterization of chicken sulfotransferases belonging to the SULT1B and SULT1C families," Arch. Biochem. Biophys., (2004), 428:1, 64-72.*
Xuan et al., "Oxidative Degradation of Bisphenol A by Crude Enzyme Prepared from Potato," J. Agri. Food Chem., (2002), 50:22, 6575-6578.*
Yoshida et al., "Oxygenation of Bisphenol A to Quinones by Polyphenol Oxidase in Vegetables," J. Agri. Food Chem., (2002), 50:15, 4377-4381.*
Hanson, D.J., "Canada Lists BPA As Toxic Compound," Chemical & Engineering News, vol. 88, No. 42, Oct. 18, 2010, Accessed at https://pubs.acs.org/cen/government/88/8842govc5.html, p. 22.*
Acevedo et al., "Degradation of polycyclic aromatic hydrocarbons by free and nanoclay-immobilized manganese peroxidase from Anthracophyllum discolor," Chemosphere, (2010), 80(3):271-278.
Cabana et al., "Immobilization of laccase from the white rot fungus Coriolopsis polyzona and use of the immobilized biocatalyst for the continuous elimination of endocrine disrupting chemicals," Bioresour Technol., (2009), 100(14):3447-3458.
Huang et al., The differences in absorption and metabolism of bisphenol A between rats and mice, Zhonghua Yu Fang Yi Xue Za Zhi, (2010), 44(8):731-735 (Abstract).
Hwang et al., "Scratch Resistant and Transparent UV-Protective Coating on Polycarbonate," Journal of Sol-Gel Science and Technology, (2003), 26:783-787.
Lloret et al., Immobilization of laccase by encapsulation in a sol-gel matrix and its characterization and use for the removal of estrogens, Biotechnol Prog., (2011), 27(6):1570-1579.
Mitsunaga et al., "Intercalated Polycarbonate/Clay Nanocomposites: Nanostructure Control and Foam Processing," Macromol. Mater. Eng., (2003), 288:543-548.
Shimizu et al., "Sulfation of bisphenol A abolished its estrogenicity based on proliferation and gene expression in human breast cancer MCF-7 cells," Toxicol. in Vitro, (2002), 16:549-556.

(Continued)

Primary Examiner — Patricia A Leith
Assistant Examiner — Erin M Bowers
(74) Attorney, Agent, or Firm — Foley & Lardner LLP

(57) ABSTRACT

Disclosed are methods, compositions and kits pertaining to polymer coatings that entrap enzymes, specifically enzymes capable of degrading bisphenol A.

22 Claims, No Drawings

(56) References Cited

OTHER PUBLICATIONS

Suiko et al., "Sulfation of Environmental Estrogen-like Chemicals by Human Cytosolic Sulfotransferases," Biochemical and Bio[hysical Research Communications, (2000), 267:80-84.

Wilson et al., "cDNA cloning, functional expression, and characterization of chicken sulfotransferases belonging to the SULT1B and SULT1C families," Arch Biochem Biophys., (2004), 428:64-72.

Xuan et al., "Oxidative Degradation of Bisphenol A by Crude Enzyme Prepared from Potato," J. Agri. Food Chem., (2002), 50:6575-6578.

Yoshida et al., "Oxygenation of Bisphenol A to Quinones by Polyphenol Oxidase in Vegetables," J. Agri. Food Chem., (2002), 50:4377-4381.

Hanson, D. J., "Canada Lists BPA As Toxic Compound," Chemical & Engineering News, vol. 88, No. 42, Oct. 18, 2010, Accessed at http://pubs.acs.org/isubscribe/journals/cen/88/i42/html/8842govc5.htm, pp. 22.

Huang, Q. and Weber, W. J. Jr., "Transformation and Removal of Bisphenol A from Aqueous Phase via Peroxidase-Mediated Oxidative Coupling Reactions: Efficacy, Products, and Pathways," Environ Sci Technol., vol. 39, No. 16, Aug. 15, 2005, pp. 6029-6036.

Hirano, T. et al., "Degradation Of Bisphenol A By The Lignin-Degrading Enzyme, Manganese Peroxidase, Produced By The White-Rot Basidiomycete, Pleurotus Ostreatus," Biosci Biotechnol Biochem., vol. 64, No. 9, Sep. 2000, pp. 1958-1962.

Huang, Q. and Weber, W. J. Jr., "Transformation And Removal Of Bisphenol A From Aqueous Phase Via Peroxidase Mediated Oxidative Coupling Reactions: Efficacy, Products, And Pathways," Environ Sci Technol., vol. 39, No. 16, Aug. 15, 2005, pp. 6029-6036.

Inoue, H. et al., "Bisphenol A glucuronidation and absorption in rat intestine," Drug Metab Dispos., vol. 31, No. 1, Jan. 2003, pp. 140-144.

Matthews, J. B. et al., "In vitro and in vivo interactions of bisphenol A and its metabolite, bisphenol A glucuronide, with estrogen receptors alpha and beta," Chem Res Toxicol., vol. 14, No. 2, Feb. 2001, pp. 149-157.

Tsutsumi, Y. et al., "Removal Of Estrogenic Activities Of Bisphenol A And Nonylphenol By Oxidative Enzymes From Lignin-Degrading Basidiomycetes," Chemosphere, vol. 42, No. 3, Jan. 2001, pp. 271-276.

Voith, M., "Removing Bisphenol A," C&EN, vol. 88, No. 43, Oct. 25, 2010, Accessed at http://cen.acs.org/articles/88/i43/Removing-Bisphenol.html, pp. 10.

Weinstein, S., "NJIT Patent May Be Able To Replace BPA; Make Consumer Products Safer," published on Feb. 24, 2010, Accessed at http://web.archive.org/web/20100707074643/http://www.njit.edu/news/2010/2010-053.php, Accessed on Jun. 27, 2014, pp. 2.

Cabana et al., "Preparation and characterization of cross-linked laccase aggregates and their application to the elimination of endocrine disrupting chemicals," J. Biotechnol., (2007), 132(1):23-31.

Gamage et al., "Human Sulfotransferasas and Their Role in Chemical Metabolism," Toxicological Sciences, (2006), 90(1):5-22.

Glad et al., "Use of silane monomers for molecular imprinting and enzyme entrapment in polysiloxane-coated porous silica," J. Chroma., (1985), 347:11-23.

Guillemette C., "Pharmacogenomics of human UDP-glucuronosyltransferase enzymes," The Pharm Jour., (2003), 3:136-158.

Hanioka et al., "Interaction of Bisphenol A with Human UDP-Glucuronosyltransferase 1A6 Enzyme," Environ Toxicol., (2008), 23:407-412.

International Search Report dated Feb. 28, 2012 in related PCT Application No. PCT/US2011/065934.

Nam et al., "Foam Processing and Cellular Structure of Polypropylene/Clay Nanocomposites," Polym. Eng. Sci., (2002), 42(9):1907-1918.

Nicolucci et al., "Biodegradation of bisphenols with immobilized laccase or tyrosinase on polyacrylonitrile beads," Biodegradation, (2011), 22(3):673-683.

Pritchett et al., "Metabolism of bisphenol A in primary cultured hepatocytes from mice, rats, and humans," Drug Metab Dispos., (2002), 30(11):1180-1185.

Sakuyama et al., "Oxidative Degradation of Alkylphenols by Horseradish Peroxidase," J Biosci. Bioeng., (2003), 96(3):227-231.

Tamura et al., "Expression Profiling of Sulfotransferases in Human Cell Lines Derived from Extra-Hepatic Tissues," Biol. Pharm. Bull., (2001), 24(11):1258-1262.

Wang et al., "Preparation of Highly Exfoliated Epoxy/Clay Nanocomposites by "Slurry Compounding": Process and Mechanisms," Langmuir, (2005), 21:3613-3618.

Watanabe et al., "Soybean Peroxidase-Catalyzed Treatment and Removal of BPA and Bisphenol Derivatives from Aqueous Solutions," Env. Prog. & Sustain Eng., (2011), 30(1):81-91.

Wydeven, T., "Plasma polymerized coating for polycarbonate: single layer, abrasion resistant, and antireflection," Applied Optics, (1977), 16(3):717-721.

Yamada et al., "Determination of optimum process parameters for peroxidase-catalysed treatment of bisphenol A and application to the removal of bisphenol derivatives," Environ Tech., (2010), 31(3):243-256.

\* cited by examiner

METHODS AND COMPOSITIONS FOR OXIDIZING BISPHENOL A

CROSS REFERENCE TO RELATED APPLICATIONS

This application is the U.S. national stage application under 35 U.S.C. §371 of International Patent Application No. PCT/US2011/065934, filed on Dec. 19, 2011, which is incorporated herein by reference in its entirety.

TECHNICAL FIELD

This disclosure relates generally to methods and compositions pertaining to chemical and enzymatic treatment of plastics and polymers. In certain embodiments, the disclosure relates to oxidation of bisphenol A that is released from plastics and polymers.

BACKGROUND

The following description is provided to assist the understanding of the reader. None of the information provided or references cited is admitted to be prior art.

Bisphenol A (BPA) is an organic molecule containing two phenol groups and two methyl groups attached to a central carbon ($HOC_6H_4$—$C(CH_3)_2C_6H_4OH$; $C_{15}H_{16}O_2$). BPA is the primary monomer component of polycarbonate plastic as well as epoxy resins. BPA-based plastics and resins are used in many different consumer plastic products, including use of epoxy resin as a protective lining for metal food and beverage cans, hard plastic bottles, food storage containers, stretchable PVC films and others. Over 8 billion pounds of BPA is produced each year and BPA has been found in human blood and urine in more than 80 biomonitoring studies.

BPA monomers can be released from epoxy resin when polymerization is incomplete and leaching of BPA increases under high heat and acidic conditions. BPA is known to bind estrogen receptors and has been shown to have effects in rodents exposed to levels of BPA similar to those seen in humans. BPA exposure in humans been suggested to contribute to several disorders, including diabetes, obesity, prostate and breast cancer, as well as infertility and genital tract abnormalities.

SUMMARY

The compositions and methods described herein relate to chemical and enzymatic treatment of plastics and polymers and involve the entrapment of enzymes in polymers.

In one aspect, the present technology provides compositions including a bisphenol A (BPA)-containing substance and at least one BPA-degrading layer adjacent to the BPA-containing substance. The BPA-degrading layer may include at least one BPA-degrading enzyme and at least one polymer.

In another aspect, the present technology provides methods of treating a bisphenol A (BPA)-containing substance. The methods may include (a) providing a BPA-containing substance; and (b) applying a BPA-degrading coating to the surface of the BPA-containing substance.

In yet another aspect, the present technology provides methods of reducing release of bisphenol A (BPA) from a BPA-containing substance. The methods may include (a) providing a BPA-containing substance and (b) applying a BPA-degrading coating to the surface of the BPA-containing substance. The BPA-degrading coating may include at least one BPA-degrading enzyme and a polymer.

As used herein, the phrase "BPA-degrading enzyme" means an enzyme that is capable of modifying BPA to reduce or eliminate its toxic qualities in mammals. For example, a peroxidase can oxidize BPA to form a polymer and 4-isopropenylphenol, neither of which has estrogenic activity. Other examples are glucuronosyltransferase, which add a glucuronosyl group to BPA and renders it more water-soluble and thus more readily excreted from the body. Similarly, sulfotransferases can sulfonate BPA, which also increases BPA's solubility and can increase its excretion from the body.

In some embodiments of the compositions and methods described herein, the BPA-containing substance is a polycarbonate plastic or an epoxy resin. In some embodiments of the compositions and methods, the BPA-degrading enzyme is entrapped in the polymer. In some embodiments of the compositions and methods, the polymer is an organic silane. In some embodiments, the organic silane is formed from the polymerization of methyltrimethoxysilane and gamma-aminopropyltriethoxysilane.

As used herein "entrapping" or "entrapment" means that a molecule is immobilized within the interstitial spaces of a porous substance, such as a polymer, and cannot easily be removed from the substance by washing or rinsing with a liquid. The entrapped molecule may not necessarily be covalently bound to the substance.

In some embodiments of the technology described herein, the BPA-degrading enzyme is oxidizes BPA. In some embodiments, the BPA-degrading enzyme includes potato enzyme extract. In some embodiments, the enzyme includes a peroxidase.

In some embodiments, the BPA-degrading enzyme adds a glucuronosyl group to BPA. In some embodiments, the BPA-degrading enzyme includes a glucuronyltransferase. In some embodiments of the compositions, the compositions and methods may include uridine diphosphate glucuronic acid (UDPGlcA).

In some embodiments of the compositions and methods described herein, the BPA-degrading enzyme adds a sulfate group to BPA. In some embodiments, the BPA-degrading enzyme may include a sulfotransferase. In some embodiments of the compositions and methods further include one or more of 3'-phosphoadenosine-5'phosphosulfate or adenosine 5'-phosphosulfate.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

In some embodiments of the aspects and embodiments disclosed herein, the BPA-degrading coating includes a BPA-degrading enzyme entrapped in a polymer particle, wherein the polymer particle forms a gel suspended in an adhesive film.

BRIEF DESCRIPTION OF THE FIGURES

No figures are included in this application.

DETAILED DESCRIPTION

Unless otherwise stated, the singular forms "a," "an," and "the" as used herein include plural reference.

Organic silane polymers can be used to form highly abrasion resistant coatings for polycarbonate surfaces. For example, hydrolyzed C1-C2 alkyltri(lower alkoxy) silane coatings can be formed on polycarbonate surfaces, by combining methyltrimethoxysilane and gamma-aminopropyltriethoxysilane. Another example of an organic silane polymer that can be used to entrap enzymes is formed from methoxytrimethylsilane and dimethyldimethoxysilane in combination with titanium oxide (Hwang et al., *J. Sol-Gel Sci. Tech.* 2003, 26: 783-787). The combination of bis(2-hydroxyethyl) aminopropyltriethoxysilane and tetraethoxysilane can also used to form a polymer that entraps enzymes.

Silane polymers that contain entrapped enzymes can also be broken up into particulates which are then combined with other polymers. For example, Hwang et al. describes making a polymer by mixing a sol of nanoparticles of titanium oxide with a sol of methoxytrimethylsilane and dimethyldimethoxysilane. *J. Sol-Gel Sci. Tech* 2003, 26: 783-787. An organic silane polymer in particulate or nanoparticle form containing entrapped enzyme could be combined with the polymer and titanium oxide sols to form a composite material with enzymatic activity. An enzyme-particulate can formulated as a sol and then mixed with other polymers, including organic silanes, to form a composite material that is resistant to wearing, scratching, and ultraviolet (UV) radiation damage.

Glucuronosyltransferases are enzymes that catalyze the transfer of glucuronosyl groups from one molecule to another. For example, uridine 5'-diphospho-glucuronosyltransferase (UDP-glucuronosyltransferase) is an enzyme that catalyzes the transfer of glucuronic acid from UDP-glucuronic acid to another molecule, such as bilirubin, androgens, estrogens, glucocorticoids, and drugs. The addition of glucuronic acid to many molecules significantly increases their water-solubility and thus much more easily removed from the body. Typically, glucuronidation by glucuronosyltransferases occurs in the intestinal tract or liver, although glucuronosyltransferases are found throughout the body. BPA has been reported to be a substrate for UDP-glucuronosyltransferase 1A6 (UGT1A6) in microsomes from human liver cells (Hanioka et al., *Environ Toxicol.* 2008 June; 23(3):407-12). In addition, BPA administration in rats has been reported to cause increases in mRNA levels of UDP-glucuronosyltransferase 2B1 (UGT2B1) and increased levels of BPA excreted in rat feces. (Huang et al., *[Chinese Journal of Preventive Medicine]*. 2010 August; 44(8):731-5).

Sulfotransferases are enzymes that catalyze the sulfonation (addition of a sulfate) of a variety of molecules. Sulfotransferases transfer sulfate groups from 3'phosphoadenosine-5'phosphosulfate (PAPS) or adenosine 5'-phosphosulfate to another molecule. Like glucuronosyltransferases, sulfotransferases have a broad range of substrate molecules which they can sulfonate depending on the subtype. Furthermore, some isoforms show binding site plasticity and can bind different shapes and types of aromatic compounds. For example, sulfotransferases (abbreviated SULT) in humans have 13 subtypes, of which SULT1A1, SULT1A2, SULT1A3, SULT1B1, SULT1C2, and SULT1C4 have been shown to sulfonate simple phenols and phenolic compounds (Gamage et al., *Toxicol. Sci.*, 2006, 90: 5-22). Sulfonation of molecules, especially non-polar lipophilic molecules, makes them highly hydrophilic and more easily solubilized and excreted by the body. Suiko et al. reported that six out of seven SULT1 enzymes tested positive for sulfonation activity using BPA as a substrate (*Biochem Biophys Res Commun.* 2000 Jan. 7; 267(1):80-4). Human HEPG2 hepatoma cells have also been shown to sulfonate environmental estrogens such as BPA (Suiko et al. *Biochem Biophys Res Commun.* 2000 Jan. 7; 267(1):80-4). BPA sulfonated by a human thermostable phenol sulfotransferase has been shown to lack estrogenic effects when given to human MCF-7 breast cancer cells (Shimizu et al., *Toxicol In Vitro.* 2002 October; 16(5):549-56.).

Laccases and tyrosinases are enzymes that are capable of oxidizing phenols, including bisphenol A. Laccases are copper-containing enzymes found in plants and fungi that can catalyze one-electron oxidation on phenols. Tyrosinase (sometimes called catechol oxidases) also contain copper and are found in plants and animals and are capable of oxidizing phenols such as tyrosine. Both laccases and tyrosinases use oxygen ($O_2$) to oxidize phenols, producing water ($H_2O$) as a byproduct.

Peroxidases are enzymes that catalyze oxidation of molecules, using peroxide compounds as electron donors to oxidize a substrate. Commonly, hydrogen peroxide is an electron donor by peroxidases, although organic hydroperoxides, such as lipid peroxides, may act as an electron donor as well. Xuan et al. described using crude potato extract to oxidize BPA to form 4[1-(4-hydroxyphenyl)-1-methyl-ethyl]benzene-1,2-diol and -1,3-diol (*J. Agric. Food Chem.* 2002, 50, 6575-6578). These oxidized products of BPA did not have estrogen-like growth-enhancing effects on human breast cancer cells (MC7) in culture. Horseradish peroxidase oxidizes BPA, resulting in polymer byproduct and 4-isopropenylphenol (Sakuyama et al., *J Biosci. Bioeng.* 2003; 96(3):227-31.). When BPA oxidized by horseradish peroxidase was tested for estrogen-like activity in medaka fish, the oxidized BPA did not increase levels of vitellogenin in the fish, indicating a lack of estrogen-like activity. Glucuronosyltransferase from cultured hepatocytes has also been reported to act on BPA to form BPA-glucuronide (Pritchett et al., *Drug Metab. Dispos.* 2002 November; 30(11):1180-5).

Enzymes have been reported to be entrapped in silane monomers while retaining their catalytic properties. The siloxane polymer produced from mixing bis(2-hydroxyethyl) aminopropyltriethoxysilane and tetraethoxysilane can be used to entrap a variety of enzymes, including glucose oxidase, trypsin, alkaline phosphatase, and horseradish peroxidase. Furthermore, entrapped enzymes retain significant levels of enzymatic activity after entrapment in polysiloxane (Glad et al., *J Chromatography* 1985; 347:11-23). Depending on whether the siloxane polymer used to entrap glucose oxidase was mixed with or without silica particles, the glucose oxidase showed activity yields between 5% and 40%. Glucose oxidase and horseradish peroxidase was also co-entrapped in polysiloxane polymer and the resulting activity yields for both enzymes showed that the enzymes were not destroyed.

Enzyme co-factors can be covalently linked to the organic silane polymer before entrapping enzymes in the polymer. For example, UDP-glucuronic acid can be covalently linked to any of the components of the organic silane before polymerizing and entrapping a UDP-glucuronosyltransferase such as UGT1A6. In addition, multiple enzymes and co-factor molecules can be entrapped using this technology. For example, both UGT1A6 and a SULT1 enzyme, as well as their co-factors UDP-glucuronic acid and PAPS could all be co-entrapped in an organic silane.

Methods for creating clear, abrasion-resistant coatings on a polycarbonate substrate have also been described. U.S. Pat. No. 4,006,271 describes creating an organic silane mixture using a hydrolyzed C1-C2 alkyltri(lower alkoxy) silane to coat polycarbonate and create a layer that is highly abrasion resistant. Hwang et al. have also shown that $TiO_2$ nanoparticles modified with 3-glycidoxypropyl-trimethoxysilane (GPTMS) and $SiO_2$ modified with acetyl acetone, mixed with methoxytrimethylsilane and dimethyldimethoxysilane can form a highly scratch-resistant and ultraviolet light-protective coating for polycarbonate (*J. Sol-Gel Sci. Tech.*, 2003, 26:783-787).

Polymerized organic silanes can also be ground into particles used as a sol-gel powder for incorporation into other polymer coatings. In another instance the particles can be nanoclay or nanoclay composites (Polym. Eng. Sci., 42(9): 1907, Macromol. Mater. Eng., 288: 543.). The silicate nanoclay can have enzyme absorbed to the surface or the surface can be silanized, epoxy coated, or epoxy silane coated (Chemosphere. 2010 June; 80(3):271-8, Langmuir. 2005 Apr. 12; 21(8):3613-8.) for covalent bond formation with the enzyme.

EXAMPLES

The present compositions, methods and kits, thus generally described, will be understood more readily by reference to the following examples, which are provided by way of illustration and are not intended to be limiting of the present methods and kits. The following is a description of the materials and experimental procedures used in the Examples.

Example 1

Entrapping UDP-Glucuronosyltransferase in an Organic Silane

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with UDP-glucuronosyltransferase 1A6 (UGT1A6), UDP-glucuronic acid, 0.25 ml. of acetic acid, 2.0 ml. ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate lens is dried for 30 minutes, then transferred to a 50° C. drying oven for 30 minutes. The polycarbonate surface is then transferred to a curing oven maintained at 100° C. for 30 minutes. Thermophiles are reported to be stable at 100° C., enzymes from thermophiles up to 109° C. (Nature Communication. 2011 Jul. 5; 2:375.). Curing temperature should be ≤100° C. in order to maintain enzyme stability until higher enzyme thermostabilities have been identified or engineered. As indicated for coating with a polycarbonate, a lower temperature cured coating (e.g. 100° C. at 30 minutes) is advantageous to ensure enzyme stability.

Example 2

Action of UDP-Glucuronosyltransferase on BPA

An organic silane layer coated on a polycarbonate surface and containing entrapped UGT1A6 and UDP-glucuronic acid is created using the method of Example 1. The amounts of UGT1A6 and UDP-glucuronic acid are adjusted such that the UGT1A6 enzyme is-co-entrapped with the UDP-glucuronic acid. When a portion of the polycarbonate polymer layer is hydrolyzed in the vicinity of the entrapped enzyme and UDP-glucuronic acid, a BPA monomer is released. The UGT1A6 enzyme then catalyzes a reaction in which the glucuronosyl group of the UDP-glucuronic acid is transferred to BPA, making it highly water soluble. The glucuronidated BPA is now in a much less toxic form, as its increased solubility greatly enhances its sequestration and excretion from the body if it is ingested.

Example 3

Forming an UGT1A6 Enzyme-Particulate-Polymer Composite

An organic silane polymer containing entrapped UGT1A6 and UDP-glucuronic acid is created using the process described in Example 1, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

Example 4

Entrapping Sulfotransferase in an Organic Silane

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with SULT1A1, 3'phosphoadenosine-5'phosphosulfate (PAPS), 0.25 ml. of acetic acid, 2.0 ml. ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate lens is dried for 30 minutes, then transferred to a 50° C. drying oven for 30 minutes. The polycarbonate surface is then transferred to a curing oven maintained at 100° C. for 30 minutes.

Example 5

Action of Sulfotransferase on BPA

An organic silane layer coated on a polycarbonate surface and containing entrapped SULT1A1 and PAPS is created using the method of Example 4. The amounts of SULT1A1 and PAPS are adjusted such that the SULT1A1 enzyme is-co-entrapped with the PAPS. When a portion of the polycarbonate polymer layer hydrolyzes in the vicinity of the entrapped enzyme and PAPS, a BPA monomer is released. The SULT1A1 enzyme then catalyzes a reaction in which the sulfate of the PAPS is transferred to BPA, making it highly water soluble. The sulfonated BPA is now in a much less toxic form, as its increased solubility greatly enhances its sequestration and excretion from the body if it is ingested.

Example 6

Forming a SULT1A1 Enzyme-Particulate-Polymer Composite

An organic silane polymer containing entrapped SULT1A1 and PAPS is created using the process described in Example 4, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

Example 7

Entrapping Potato Enzyme Extract in an Organic Silane

Potato enzyme extract is prepared by homogenizing potato in 10 volumes of cold acetone (−30° C.), then washing with acetone and water. The extract is then filtered and dried overnight. The dried residue is then homogenized with 10 volumes of a solution containing 50 mM citric acid and 100 mM phosphate buffer (pH 7.0) for 10 minutes at 4° C. The homogenate is then centrifuged at 10,000 g for 10 minutes and the supernatant is removed. The supernatant contains crude potato enzymes.

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with potato enzyme extract, 0.25 ml of acetic acid, 2.0 ml ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate lens is dried for 30 minutes, then transferred to a 50° C. drying oven for 30 minutes. The polycarbonate surface is then transferred to a curing oven maintained at 100° C. for 30 minutes.

Example 8

Action of Potato Enzyme Extract on BPA

An organic silane layer coated on a polycarbonate surface and containing entrapped potato enzyme extract is created using the method of Example 7. When a portion of the polycarbonate polymer layer hydrolyzes in the vicinity of the entrapped potato enzyme extract, a BPA monomer is released. The enzyme extract then catalyzes a reaction in which the BPA molecule is oxidized, greatly reducing the estrogen-like activity relative to the non-oxidized BPA and thus rendering it less toxic.

Example 9

Forming a Potato Enzyme Extract-Particulate-Polymer Composite

An organic silane polymer containing entrapped potato enzyme extract is created using the process described in Example 7, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

Example 10

Entrapping Laccase in an Organic Silane

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with laccase, 0.25 ml of acetic acid, 2.0 ml ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate lens is dried for 30 minutes, then transferred to a 50° C. drying oven for 30 minutes. The polycarbonate surface is then transferred to a curing oven maintained at 100° C. for 30 minutes.

Example 11

Action of Laccase on BPA

An organic silane layer coated on a polycarbonate surface and containing entrapped laccase is created using the method of Example 9. When a portion of the polycarbonate polymer layer hydrolyzes in the vicinity of the entrapped laccase enzyme, a BPA monomer is released. The laccase enzyme then catalyzes a reaction in which the BPA molecule is oxidized, greatly reducing the estrogen-like activity relative to the non-oxidized BPA and thus rendering it less toxic.

Example 12

Forming a Laccase-Particulate-Polymer Composite

An organic silane polymer containing entrapped laccase enzyme is created using the process described in Example 1, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

Example 13

Entrapping a Peroxidase in an Organic Silane

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with horseradish peroxidase, 0.25 ml of acetic acid, 2.0 ml ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate lens is dried for 30 minutes, then transferred to a 50° C. drying oven for 30 minutes. The polycarbonate surface is then transferred to a curing oven maintained at 100° C. for 30 minutes.

Example 14

Action of Peroxidase on BPA

An organic silane layer coated on a polycarbonate surface and containing entrapped laccase is created using the method of Example 13. When a portion of the polycarbonate polymer layer hydrolyzes in the vicinity of the entrapped peroxidase enzyme, a BPA monomer is released. The peroxidase enzyme then catalyzes a reaction in which the BPA molecule is oxidized, greatly reducing the estrogen-like activity relative to the non-oxidized BPA and thus rendering it less toxic.

Example 15

Forming a Laccase-Particulate-Polymer Composite

An organic silane polymer containing entrapped peroxidase enzyme is created using the process described in Example 13, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition comprising:
    a bisphenol A (BPA)-containing substance; and
    at least one BPA-degrading layer coated onto the BPA-containing substance, wherein the BPA-degrading layer comprises a sol and a plurality of polymer particles embedded in the sol, wherein BPA-degrading enzymes are entrapped in the polymer particles, and wherein the polymer particles comprise an organic silane formed from polymerization of methyltrimethoxysilane and gamma-aminopropyltriethoxysilane.

2. The composition of claim 1, wherein the BPA-containing substance comprises a polycarbonate plastic or an epoxy resin.

3. The composition of claim 1, wherein the BPA-degrading enzyme oxidizes BPA.

4. The composition of claim 1, wherein the BPA-degrading enzyme is one or more selected from the group consisting of a potato enzyme extract, a laccase, a tyrosinase, or a peroxidase.

5. The composition of claim 1, wherein the BPA-degrading enzyme comprises a glucuronosyltransferase.

6. The composition of claim 1, wherein the BPA-degrading enzyme comprises a sulfotransferase.

7. A method of treating a bisphenol A (BPA)-containing substance, the method comprising:
    applying a BPA-degrading coating to a surface of a BPA-containing substance, wherein the BPA-degrading coating comprises a sol and a plurality of polymer particles embedded in the sol, wherein BPA-degrading enzymes are entrapped in the polymer particles, and wherein the polymer particles comprise an organic silane formed from polymerization of methyltrimethoxysilane and gamma-aminopropyltriethoxysilane.

8. The method of claim 7, wherein applying the BPA-degrading coating comprises applying a BPA-degrading coating comprising BPA-degrading enzymes entrapped in polymer particles, wherein the polymer particles form a gel suspended in an adhesive film.

9. The method of claim 7, wherein applying the BPA-degrading coating to the surface of the BPA-containing substance comprises applying a BPA-degrading coating to a BPA-containing substance selected from a polycarbonate plastic and/or an epoxy resin.

10. The method of claim 7, wherein applying the BPA-degrading coating to the surface of the BPA-containing substance comprises applying a BPA-degrading coating comprising a BPA-degrading enzyme that oxidizes BPA.

11. The method of claim 7, wherein applying the BPA-degrading coating to the surface of the BPA-containing substance comprises applying a BPA-degrading coating comprising at least one BPA-degrading enzyme selected from a potato enzyme extract, a laccase, a tyrosinase, or a peroxidase.

12. The method of claim 7, wherein applying the BPA-degrading coating to the surface of the BPA-containing substance comprises applying a BPA-degrading coating comprising a glucuronosyltransferase.

13. The method of claim 7, wherein applying the BPA-degrading coating to the surface of the BPA-containing substance comprises applying a BPA-degrading coating comprising a sulfotransferase.

14. A method of reducing release of bisphenol A (BPA) from a BPA-containing substance comprising:
applying a BPA-degrading coating to a surface of a BPA-containing substance, wherein the BPA-degrading coating comprises a sol and a plurality of polymer particles embedded in the sol, wherein BPA-degrading enzymes are entrapped in the polymer particles, and wherein the polymer particles comprise an organic silane formed from polymerization of methyltrimethoxysilane and gamma-aminopropyltriethoxysilane.

15. The method of claim 14, wherein applying the BPA-degrading coating comprises applying a BPA-degrading coating comprising BPA-degrading enzymes entrapped in polymer particles, wherein the polymer particles form a gel suspended in an adhesive film.

16. The method of claim 14, wherein applying the BPA-degrading coating to the surface of the BPA-containing substance comprises applying a BPA-degrading coating to a BPA-containing substance selected from a polycarbonate plastic and/or an epoxy resin.

17. The method of claim 14, wherein applying the BPA-degrading coating to the surface of the BPA-contain substance comprises applying a BPA-degrading coating comprising a BPA-degrading enzyme that oxidizes BPA.

18. The method of claim 14, wherein applying the BPA-degrading coating to the surface of the BPA-contain substance comprises applying a BPA-degrading coating comprising at least one BPA-degrading enzyme selected from a potato enzyme extract, a laccase, a tyrosinase, or a peroxidase.

19. The method of claim 14, wherein applying the BPA-degrading coating to the surface of the BPA-containing substance comprises applying a BPA-degrading coating comprising a glucuronosyltransferase.

20. The method of claim 14, wherein applying the BPA-degrading coating to the surface of the BPA-containing substance comprises applying a BPA-degrading coating comprising a sulfotransferase.

21. The composition of claim 1, wherein the sol comprises one or more sols selected from the group consisting of sol of titanium oxide, sol of methoxytrimethylsilane, and sol of dimethyldimethoxysilane.

22. The composition of claim 1, wherein the polymer particles comprise nanoparticles.

* * * * *